(12) United States Patent
Afzali-Ardakani et al.

(10) Patent No.: US 8,039,909 B2
(45) Date of Patent: Oct. 18, 2011

(54) SEMICONDUCTOR NANOWIRES CHARGE SENSOR

(75) Inventors: Ali Afzali-Ardakani, Ossining, NY (US); Lidija Sekaric, Mount Kisco, NY (US); George S. Tulevski, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 12/324,219

(22) Filed: Nov. 26, 2008

(65) Prior Publication Data

US 2010/0129925 A1 May 27, 2010

(51) Int. Cl.
*H01L 27/14* (2006.01)
(52) U.S. Cl. ........... 257/414; 257/253; 422/82.02
(58) Field of Classification Search ........... 257/414, 257/253; 422/82.02
See application file for complete search history.

(56) References Cited

U.S. PATENT DOCUMENTS

| | | | |
|---|---|---|---|
| 6,528,020 B1* | 3/2003 | Dai et al. ............ | 422/98 |
| 6,894,359 B2* | 5/2005 | Bradley et al. .......... | 257/414 |
| 7,129,554 B2 | 10/2006 | Lieber et al. | |
| 7,531,136 B2* | 5/2009 | Besnard et al. ........ | 422/82.02 |
| 7,544,978 B2* | 6/2009 | Noy et al. ............ | 257/213 |
| 2004/0136866 A1 | 7/2004 | Pontis et al. | |
| 2004/0169243 A1* | 9/2004 | Tao et al. ............ | 257/414 |
| 2006/0131574 A1 | 6/2006 | Yu et al. | |
| 2006/0237805 A1* | 10/2006 | Segal et al. ............ | 257/414 |
| 2007/0132043 A1* | 6/2007 | Bradley et al. .......... | 257/414 |
| 2007/0224804 A1* | 9/2007 | Tiano et al. ............ | 438/618 |
| 2008/0031034 A1 | 2/2008 | Jalabert | |
| 2008/0211040 A1 | 9/2008 | Lieber et al. | |
| 2008/0218740 A1* | 9/2008 | Williams et al. ........ | 356/72 |
| 2008/0224717 A1 | 9/2008 | Kim et al. | |
| 2008/0229839 A1 | 9/2008 | Chakraborty | |
| 2010/0044225 A1* | 2/2010 | Kim et al. ............ | 204/403.15 |

OTHER PUBLICATIONS

Wang et al., "Silicon-based nanochannel glucose sensor", Applied Physics Letters 92, 2008, pp. 013903-1-013903-3, American Institute of Physics.

* cited by examiner

*Primary Examiner* — Steven Fulk
(74) *Attorney, Agent, or Firm* — Scully, Scott, Murphy & Presser, P.C.; Louis J. Percello, Esq.

(57) ABSTRACT

A semiconductor nanowire is coated with a chemical coating layer that comprises a functional material which modulates the quantity of free charge carriers within the semiconductor nanowire. The outer surface of the chemical coating layer includes a chemical group that facilitates bonding with molecules to be detected through electrostatic forces. The bonding between the chemical coating layer and the molecules alters the electrical charge distribution in the chemical coating layer, which alters the amount of the free charge carriers and the conductivity in the semiconductor nanowire. The coated semiconductor nanowire may be employed as a chemical sensor for the type of chemicals that bonds with the functional material in the chemical coating layer. Detection of such chemicals may indicate pH of a solution, a vapor pressure of a reactive material in gas phase, and/or a concentration of a molecule in a solution.

20 Claims, 7 Drawing Sheets

SEMICONDUCTOR NANOWIRES CHARGE SENSOR

FIELD OF THE INVENTION

The present invention relates to semiconductor devices, and particularly to a semiconductor nanowire charge sensor that detects chemicals through electrical charges induced in a semiconductor wire, methods of manufacturing the same, and methods of operating the same.

BACKGROUND OF THE INVENTION

A semiconductor nanowire refers to a semiconductor wire having transverse lateral and vertical dimensions of the order of a nanometer ($10^{-9}$ meter) or tens of nanometers. Typically, the transverse lateral dimension and the vertical dimension are less than 20 nm but can be as large as 100 nm.

The limitation on the lateral dimension applies to the transverse lateral dimension (the width) and the vertical lateral dimension (the height). The longitudinal lateral dimension (the length) of the semiconductor nanowire is unlimited, and may be, for example, from 1 nm to 1 mm. (The preferred length is less than 1 um) When the lateral dimensions of the semiconductor nanowire is less than tens of nanometers, quantum mechanical effects may become important. As such, semiconductor nanowires are also called semiconductor quantum wires.

The transverse lateral dimension of a semiconductor nanowire is currently sublithographic, i.e., may not be printed by a direct image transfer from a photoresist that is patterned by a single exposure. As of 2008, the critical dimension, i.e., the smallest printable dimension that may be printed by lithographic methods, is about 35 nm. Dimensions less than the critical dimension are called sublithographic dimensions. At any given time, the critical dimension and the range of the sublithographic dimension are defined by the best available lithographic tool in the semiconductor industry. In general, the critical dimension and the range of the sublithographic dimension decreases in each successive technology node and established by a manufacturing standard accepted across the semiconductor industry.

The charge transport property of a semiconductor nanowire is controlled by the charge carriers present in the semiconductor nanowire. A higher density of free charge carriers in the semiconductor nanowire increases the conductivity of the semiconductor nanowire, while a low density of free charge carriers in the semiconductor nanowire decreases the conductivity of the semiconductor nanowire.

SUMMARY OF THE INVENTION

A semiconductor nanowire is coated with a chemical coating layer that modulates the quantity of free charge carriers within the semiconductor nanowire. The chemical coating layer comprises a functional material that affects the amount of free charge carriers in the semiconductor substrate. The inner surface of the chemical coating layer includes a chemical group that facilitates bonding with molecules to be detected through electrostatic forces. The bonding between the chemical coating layer and the molecules alters the electrical charge distribution in the chemical coating layer, which alters the amount of the free charge carriers and the conductivity in the semiconductor nanowire. The coated semiconductor nanowire may be employed as a chemical sensor for a type of chemicals that bonds with the functional material in the chemical coating layer. Detection of such chemicals may indicate pH of a solution, a vapor pressure of a reactive material in gas phase, and/or a concentration of a molecule in a solution.

According to an aspect of the present invention, a semiconductor device is provided, which includes: a semiconductor nanowire located on a substrate and comprising a semiconductor material; and a chemical coating layer located on the semiconductor nanowire and comprising a functional material that bonds with at least one type of charged molecule, wherein free charge carrier density in the semiconductor nanowire is altered upon bonding of the at least one type of charged molecule and the functional material.

According to another aspect of the present invention, a chemical detector is provided, which includes: a semiconductor nanowire located on a substrate and comprising a semiconductor material; and a chemical coating layer located on the semiconductor nanowire and comprising a functional material that bonds with at least one type of chemical molecule, wherein free charge carrier density in the semiconductor nanowire is altered upon bonding of the at least one type of chemical molecule and the functional material, and wherein presence or concentration of the at least one type of chemical molecule is detected by measuring conductivity of the semiconductor nanowire.

According to yet another aspect of the present invention, a method of forming a chemical detector is provided, which includes: forming a semiconductor nanowire comprising a semiconductor material on a substrate; and forming a chemical coating layer on the semiconductor nanowire, wherein the chemical coating layer comprises a functional material that bonds with at least one type of chemical molecule, wherein free charge carrier density in the semiconductor nanowire is altered upon bonding of the at least one type of chemical molecule and the functional material.

According to still another aspect of the present invention, a method of operating a chemical detector is provided, which includes: providing a chemical detector including a semiconductor nanowire located on a substrate and comprising a semiconductor material and a chemical coating layer located on the semiconductor nanowire and comprising a functional material that bonds with at least one type of chemical molecule; placing the chemical detector in a fluid ambient containing the at least one type of chemical molecule, wherein free charge carrier density in the semiconductor nanowire is altered upon bonding of the at least one type of chemical molecule and the functional material; and measuring a resistance of the semiconductor nanowire.

BRIEF DESCRIPTION OF THE DRAWINGS

FIGS. 1A-1C are various views of an exemplary semiconductor device according to the present invention after patterning of a semiconductor nanowire and first and second semiconductor pads. FIG. 1A is a top-down view, FIG. 1B is a vertical cross-sectional view along the plane B-B' in FIG. 1A, and FIG. 1C is a vertical cross-sectional view along the plane C-C' in FIG. 1A.

FIGS. 2A-2C are various views of an exemplary semiconductor device according to the present invention after undercutting a buried insulator material from underneath the semiconductor nanowire. FIG. 2A is a top-down view, FIG. 2B is a vertical cross-sectional view along the plane B-B' in FIG. 2A, and FIG. 2C is a vertical cross-sectional view along the plane C-C' in FIG. 2A.

FIGS. 3A-3C are various views of an exemplary semiconductor device according to the present invention after formation of contact vias. FIG. 3A is a top-down view, FIG. 3B is a vertical cross-sectional view along the plane B-B' in FIG. 3A, and FIG. 3C is a vertical cross-sectional view along the plane C-C' in FIG. 3A.

FIGS. 4A-4C are various views of an exemplary semiconductor device according to the present invention after formation of a chemical coating layer. FIG. 4A is a top-down view, FIG. 4B is a vertical cross-sectional view along the plane B-B' in FIG. 4A, and FIG. 4C is a vertical cross-sectional view along the plane C-C' in FIG. 4A.

DETAILED DESCRIPTION OF THE INVENTION

As stated above, the present invention relates to a semiconductor nanowire charge sensor that detects chemicals through electrical charges induced in a semiconductor wire, methods of manufacturing the same, and methods of operating the same, which are now described in detail with accompanying figures. It is noted that like and corresponding elements are referred to by like reference numerals.

Figure 1A:
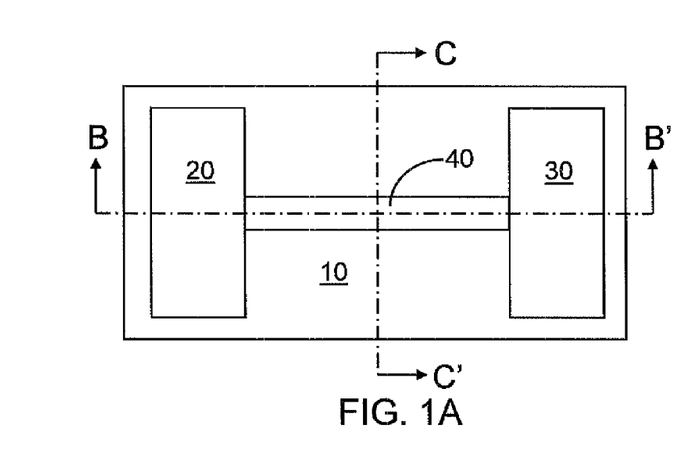
Figure 1B:
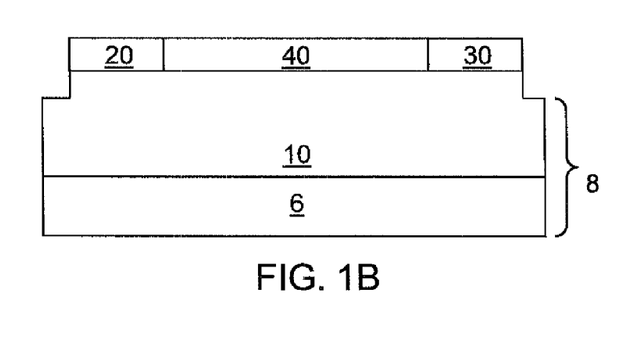
Figure 1C:
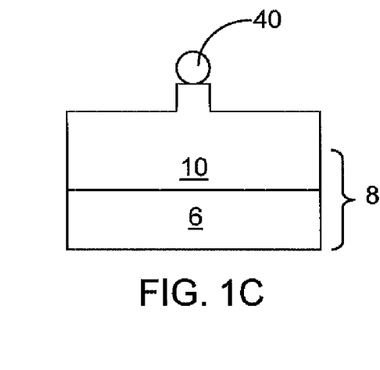

Referring to FIGS. 1A-1C, an exemplary semiconductor structure according to the present invention includes a substrate 8 which contains a handle substrate 6 and an insulator layer 10. A semiconductor nanowire 40 comprising a semiconductor material is formed over the substrate 8. A first semiconductor pad 20 and a second semiconductor pad 30 that comprise a semiconductor material are formed on the substrate 8 such that the first and second semiconductor pads (20, 30) laterally abut a first end portion of the semiconductor nanowire 40 and a second end portion of the semiconductor nanowire 40, respectively.

The semiconductor nanowire 40 and the first and second semiconductor pads (20, 30) may be formed from a semiconductor layer by methods known in the art. For example, a semiconductor-on-insulator (SOI) layer comprising a handle substrate 6, a buried insulator layer, and a top semiconductor layer may be provided for the purposes of the present invention. The top semiconductor layer may be patterned to form the semiconductor nanowire and the first and second semiconductor pads (20, 30). As the top surface of the buried insulator layer becomes exposed after patterning of the top semiconductor layer, the buried insulator layer becomes the insulator layer 10.

The top semiconductor layer comprises a semiconductor material, which may be selected from, but is not limited to silicon, germanium, silicon-germanium alloy, silicon carbon alloy, silicon-germanium-carbon alloy, gallium arsenide, indium arsenide, indium phosphide, III-V compound semiconductor materials, II-VI compound semiconductor materials, organic semiconductor materials, and other compound semiconductor materials. In one embodiment, the top semiconductor layer may include a Si-containing semiconductor material such as single crystalline silicon or a single crystalline silicon-germanium alloy. The semiconductor nanowire 40 and the first and second semiconductor pads (20, 30) have the same composition as the top semiconductor layer. If the semiconductor layer comprises a single crystalline semiconductor material, the entirety of the semiconductor nanowire 40 and the first and second semiconductor pads (20, 30) is a single crystalline semiconductor material having an epitaxial alignment throughout. The first and second semiconductor pads (20, 30) have a thickness greater than the vertical dimension of the semiconductor nanowire 40.

The semiconductor nanowire 40 has a free charge carrier density determined by the free charge carrier concentration. In an unperturbed state, the free charge carrier concentration is determined by the dopant concentration in the semiconductor nanowire 40 and the surrounding pads 20 and 30.

In one case, the semiconductor nanowire 40 comprises a p-doped semiconductor material and the free charge carrier density is substantially the same as the density of holes in the p-doped semiconductor material of the semiconductor nanowire 40. This is because the minority charge carrier concentration, i.e., the density of electrons, is many orders of magnitude smaller than the density of holes in this case. In other words, the density of holes in the p-doped semiconductor material is substantially the same as the density of p-type dopant atoms in the p-doped semiconductor material of the semiconductor nanowire 40. Typically, the dopant concentration in the semiconductor nanowire 40 is from $1.0 \times 10^{15}/cm^3$ to $1.0 \times 10^{19}/cm^3$, although lesser and greater dopant concentrations are also contemplated herein. The first and second semiconductor pads (20, 30) can be heavily doped with p-type or n-type dopants. Typically, the dopant concentration of the first and second semiconductor pads (20, 30) is from $1.0 \times 10^{19}/cm^3$ to $1.0 \times 10^{21}/cm^3$ in this case, although lesser and greater dopant concentrations are also contemplated herein.

In another case, the semiconductor nanowire 40 comprises an n-doped semiconductor material and the free charge carrier density is substantially the same as the density of electrons in the n-doped semiconductor material of the semiconductor nanowire 40. This is because the Minority charge carrier concentration, i.e., the density of holes, is many orders of magnitude smaller than the density of electrons in this case. In other words, the density of electrons in the n-doped semiconductor material is substantially the same as the density of n-type dopant atoms in the n-doped semiconductor material of the semiconductor nanowire 40. Typically, the dopant concentration in the semiconductor nanowire 40 is from $1.0 \times 10^{15}/cm^3$ to $1.0 \times 10^{19}/cm^3$, although lesser and greater dopant concentrations are also contemplated herein. The first and second semiconductor pads (20, 30) are doped with n-type or p-type dopants. Typically, the dopant concentration of the first and second semiconductor pads (20, 30) is from $1.0 \times 10^{19}/cm^3$ to $1.0 \times 10^{21}/cm^3$ in this case, although lesser and greater dopant concentrations are also contemplated herein.

In yet another case, the semiconductor nanowire 40 comprises a substantially intrinsic semiconductor material and the free charge carrier density is the sum of the density of electrons and the density of holes in the substantially intrinsic semiconductor material of the semiconductor nanowire 40. In this case, the dopant concentration in the semiconductor nanowire 40 is less than $1.0 \times 10^{15}/cm^3$, and is typically less than $1.0×10^{14}/cm^3$. The first and second semiconductor pads (20, 30) may be doped with n-type dopants or p-type dopants to provide a conductivity that is orders of magnitude higher than the conductivity of the semiconductor nanowire 40. If the semiconductor nanowire 40 is substantially intrinsic and has a low conductivity, i.e. high resistivity, the type of doping for the first and second semiconductor pads (20, 30) is not essential because the electrical characteristic of the conduction path including the first semiconductor pad 20, the semiconductor nanowire 40, and the second semiconductor nanowire 30 is resistive due to the high resistance of the semiconductor nanowire 40. Typically, the dopant concentration of the first and second semiconductor pads (20, 30) is from $1.0×10^{19}/cm^3$ to $1.0×10^{21}/cm^3$ in this case, although lesser and greater dopant concentrations are also contemplated herein.

The insulator layer 10 is a dielectric material layer, i.e., a layer including a dielectric material. The dielectric material of the insulator layer 10 may be, for example, silicon oxide, silicon nitride, silicon oxynitride, quartz, a ceramic material, or a combination thereof. The thickness of the insulator layer 10 may be from 50 nm to 1,000 nm, although lesser and greater thicknesses are also contemplated herein. The handle substrate 6 may comprise a semiconductor material, an insulator material, or a conductive material. In some cases, the handle substrate 6 and the insulator layer 10 may comprise the same dielectric material and may be of unitary and integral construction.

The semiconductor nanowire 40 and the first and second semiconductor pads (20, 30) may be formed, for example, by lithographic patterning employing photolithography and an anisotropic etch. For example, shapes corresponding to the semiconductor nanowire 40 and the first and second semiconductor pads (20, 30) may be patterned in a photoresist (not shown). The pattern in the photoresist is subsequently transferred by an anisotropic etch into the top semiconductor layer to form the semiconductor nanowire 40 and the first and second semiconductor pads (20, 30). Optionally, the edges of the semiconductor nanowire 40 may be rounded during further thinning of the wire (to get sub-lithographic dimensions).

The cross-sectional area of the semiconductor nanowire 40 in the C-C' plane may be rectangular, circular, elliptical, or a shape that may be formed by at least one curvilinear shape and/or at least one polygonal shape. Preferably, the cross-sectional area of the semiconductor nanowire 40 is substantially circular, and has a dimension less than 20 nm.

Figure 2A:
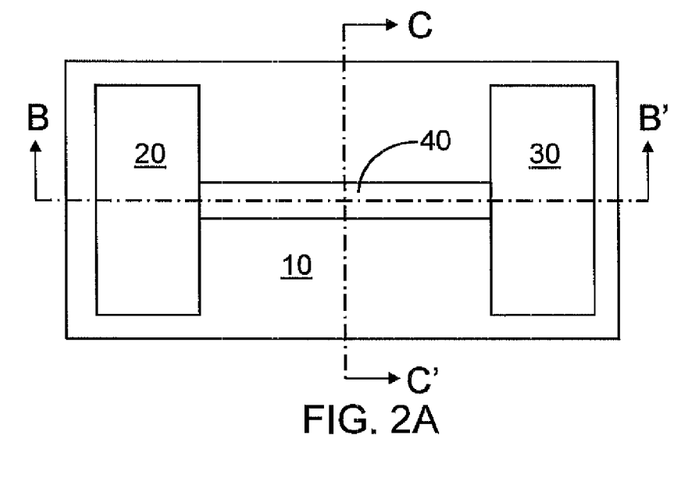
Figure 2B:
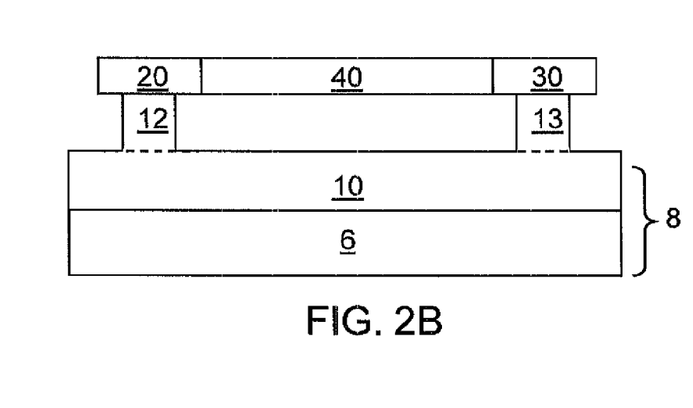
Figure 2C:
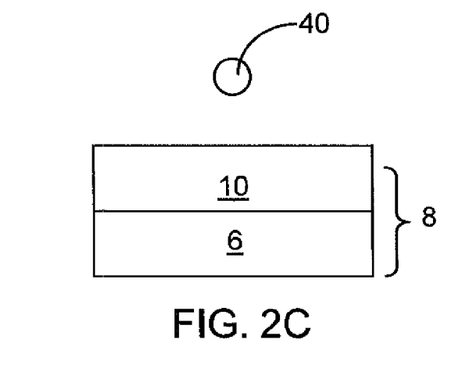

Referring to FIGS. 2A-2C, a substantially isotropic etch is performed on the dielectric material of the insulator layer 10 selective to the semiconductor material of the semiconductor nanowire 40 and the first and second semiconductor pads (20, 30). The semiconductor nanowire 40 and the first and second semiconductor pads (20, 30) are employed as an etch mask for the substantially isotropic etch. The substantially isotropic etch may be a wet etch or a dry etch. Because the etch is substantially isotropic, the semiconductor nanowire 40 and the edges of the first and second semiconductor pads (20, 30) are undercut as the etch progresses. The etch proceeds at least until the portion of the insulator layer 10 located directly underneath semiconductor nanowire 40 is removed. The semiconductor nanowire becomes suspended over the substrate 8 and does not directly contact the substrate 8. In other words, the semiconductor nanowire 40 does not have direct physical contact with the remaining portions of the insulator layer 10.

The etch also removes the dielectric material of the insulator layer 10 from underneath the peripheral portions of the first semiconductor pad 20 and the second semiconductor pad 30. A first insulator pedestal 12 comprising a remaining portion of the insulator layer 10 is formed directly underneath a center portion of the first semiconductor pad 20. Likewise, a second insulator pedestal 13 comprising another remaining portion of the insulator layer 10 is formed directly underneath a center portion of the second semiconductor pad 30. The first insulator pedestal 12 and the second insulator pedestal 13 are of integral construction with the insulator layer 10 and have the same composition as the insulator layer 10.

The semiconductor nanowire 40 may be thinned to reduce the lateral width to a sublithographic dimension, i.e., a dimension that may not be printed directly by lithographic techniques. In case the width of the semiconductor nanowire 40 is a sublithographic dimension, which may be, for example, from 1 nm to 20 nm.

If additional thinning is employed to provide a sublithographic dimension for the lateral width of the semiconductor nanowire 40, the additional thinning may employ thermal conversion of the surface of the semiconductor nanowire 40 into a dielectric material such as a semiconductor oxide, a semiconductor nitride, or a semiconductor oxynitride, followed by removal of the dielectric material. For example, if the semiconductor nanowire 40 includes silicon, the semiconductor oxide material may be silicon oxide, which may be removed by hydrofluoric acid (HF). Alternately or in conjunction, a substantially isotropic etch may be employed to thin the semiconductor nanowire 40 to a sublithographic dimension.

Figure 3A:
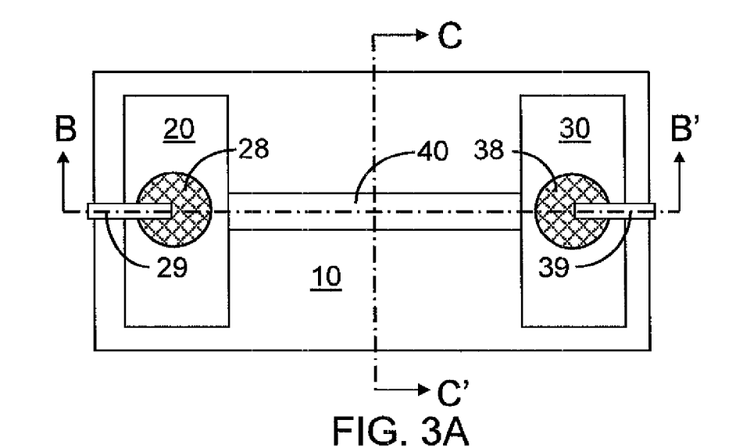
Figure 3B:
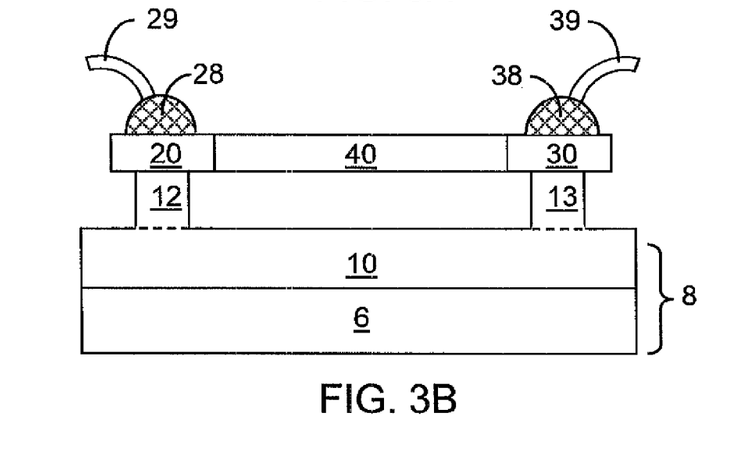
Figure 3C:
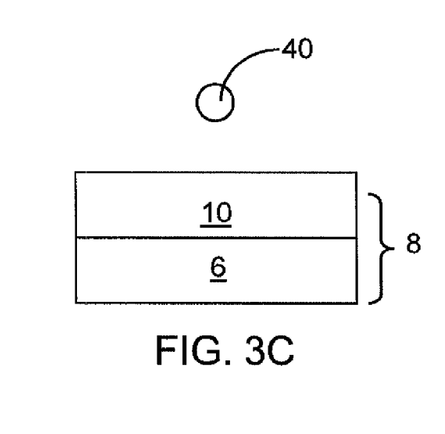

Referring to FIGS. 3A-3C, a first contact structure 28, a second contact structure 38, a first lead wire 29, and a second lead wire 39 are formed utilizing methods known in the art. The first contact structure 28 is formed directly on the first semiconductor pad 20. The second contact structure 38 is formed directly on the second semiconductor pad 30. The first lead wire 29 is formed directly on the first semiconductor pad 20. The second lead wire 39 is formed directly on the second semiconductor pad 30. The first contact structure 28, the second contact structure 38, the first lead wire 29, and the second lead wire 39 collectively enable the measurement of the resistance of the conductive path including the first semiconductor pad 20, the semiconductor nanowire 40, and the second semiconductor pad 30. For example, the first contact structure 28 and the second contract structure 38 may be solder balls, which typically have a lateral dimension from 40 microns to 200 microns. Alternately, the first contact structure 28 and the second contract structure 38 may be a metal-semiconductor alloy pad or a metallic pad having a lateral dimension on the order of 100 microns to enable contact with a test probe. The first lead wire 29 and the second lead wire 39 may be replaced with electrical probes.

Figure 4A:
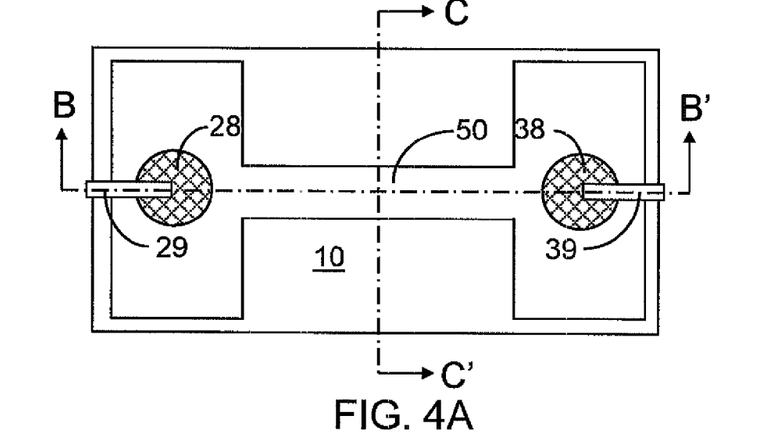
Figure 4B:
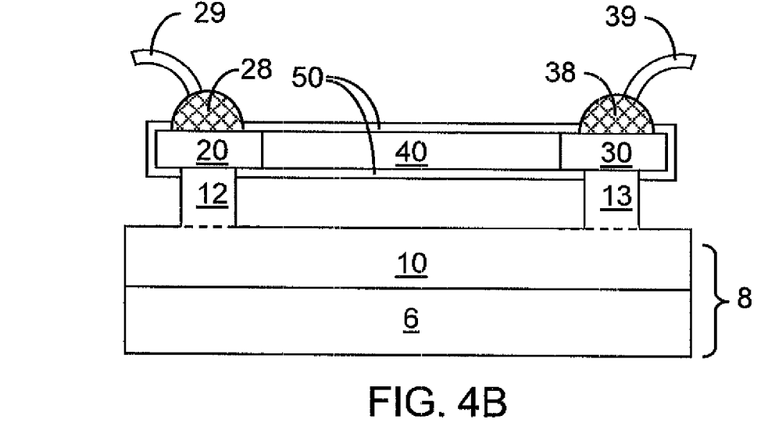
Figure 4C:
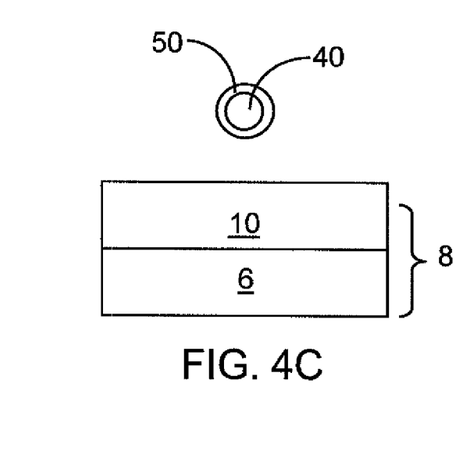

Referring to FIGS. 4A-4C, a chemical coating layer 50 is formed on the exposed surfaces of the semiconductor nanowire 40. The chemical coating layer 50 may be formed, for example, by dipping the exemplary semiconductor structure in a solution containing the chemical for the chemical coating layer 50. Alternately, the chemical coating layer 50 may be formed by vapor deposition or by a spray.

The chemical coating layer 50 is formed directly on the semiconductor nanowire 40 and includes a functional material that bonds with at least one type of charged molecule. The charged molecule may be positively charged or negatively charged. Upon bonding of the at least one type of charged molecule and the functional material in the chemical coating layer, the free charge carrier density in the semiconductor nanowire 50 is altered.

The chemical coating layer 50 will be formed on the entirety of the semiconductor nanowire 40. The chemical property of the chemical coating layer 50 is such that the chemical coating layer 50 will not be formed on the exposed surfaces of the insulator layer 20. The chemical coating layer 50, the first semiconductor pad 20, and the second semiconductor pad 30 encapsulate the semiconductor nanowire 40.

For example, the functional material of the chemical coating layer 50 may include a semiconductor-bound functionalizing molecule that is self-aligned in the chemical coating layer 50. A semiconductor-bound functionalizing molecule, as defined in the present invention, is a molecule that selectively binds to only to the semiconductor material that the nanowire is made from (such as hydrogen-terminated silicon). It may have a non-zero electrical dipole moment. In other words, the center of positive charge distribution weighted by the probability of the presence of the positive charge is not the same as the center of negative charge distribution weighted by the probability of the presence of the negative charge in such molecule. Exemplary molecules include, but are not limited to, pyridine, dipyridine, or terpyridine, a boronic acid. In this case, a functional group in the molecule that will attach to the charged species of interest is exposed on an exterior surface of the chemical coating layer 50. The functional group bonds with the at least one type of charged molecule.

Figure 5:
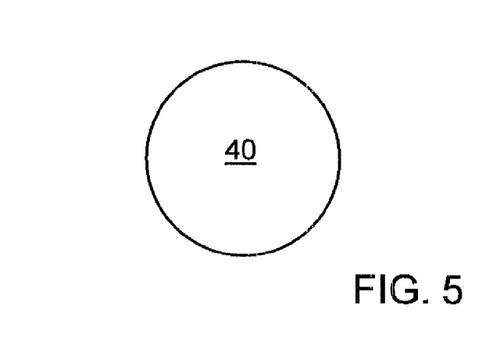
FIG. 5 is a magnified vertical cross-sectional view of the exemplary semiconductor structure along the plane C-C' prior to formation of a chemical coating layer.
Figure 6:
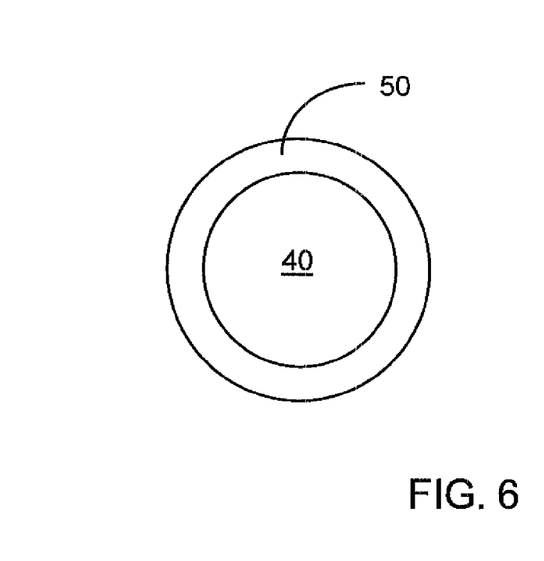
FIG. 6 is a magnified vertical cross-sectional view of the exemplary semiconductor structure along the plane C-C' after formation of the chemical coating layer.

This type of chemical reaction is illustrated in FIGS. 5-8, which schematically shows molecular alignment of the functionalizing molecules 50A and charged molecules 60. FIG. 5 shows a magnified vertical cross-sectional view of the semiconductor nanowire 40 along the plane C-C' at a processing step corresponding to FIGS. 3A-3C, which is prior to formation of the chemical coating layer 50. FIG. 6 shows a magnified vertical cross-sectional view of the exemplary semiconductor structure along the plane C-C' at a processing step corresponding to FIGS. 4A-4C, which is after formation of the chemical coating layer 50.

Figure 7:
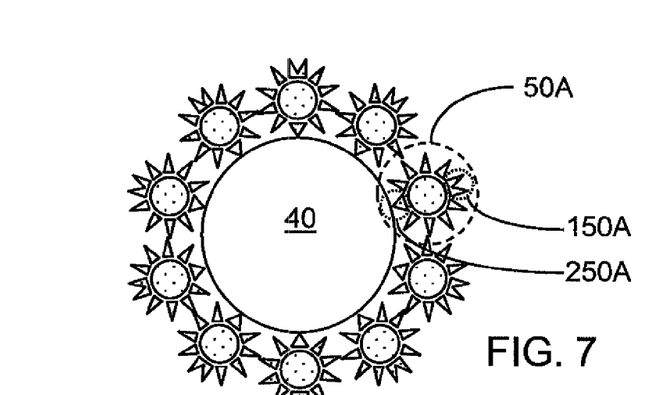
FIG. 7 is a schematic view showing atomic arrangement of semiconductor-bound functionalizing molecules of a functional material in the chemical coating layer.

FIG. 7 illustrates molecular alignment of the functionalizing molecules 50A within the chemical coating layer 50. In this illustrative example, the chemical coating layer 50 is a monolayer of the functionalizing molecules 50A. The functional material is the semiconductor-bound molecules 50A.

In this illustrative example, each functionalizing molecule 50A includes a first functional group 150A and a second functional group 250A. In this case, each functionalizing molecule 50A may be self-aligned on the surface of the semiconductor nanowire 40 so that the first functional group 150A is on an exterior surface of the chemical coating layer 50. Non-limiting examples of the first functional group 150A include pyridine, dipyridyl, terpyridine, porphyrine, organic acids like boronic acid, phosphonic acid, sulfonic acid, unsaturated imides such as maleimide, and fluorinated alcohols such as hexafluoroisopropanol. The second functional group 250A bonds to the surface of the semiconductor nanowire 40. Non-limiting examples of the second functional group 150A include diazonium salts, thiols, alcohols, alkenes, and alkynes.

In general, the second functional group 250A is located in closer proximity to the semiconductor nanowire 40 than the first functional group 150A in each functionalizing molecule 50A. If the first functional group 250A is directly bonded to the surface of the semiconductor nanowire 40 and the second functional group 150A is located on the exterior surface of the chemical coating layer 50, the direction along the first functional group 150A and the second functional group 250A in the functionalizing molecule 50A may be a radial direction from a coaxial center line of the semiconductor nanowire 40 but need not be. The coaxial center line runs along the direction connecting the first semiconductor pad 20 and the second semiconductor pad 30. If the semiconductor nanowire 40 has a circular cross-sectional area, the radial directions converge on the coaxial center line of the semiconductor nanowire 40.

Figure 8:
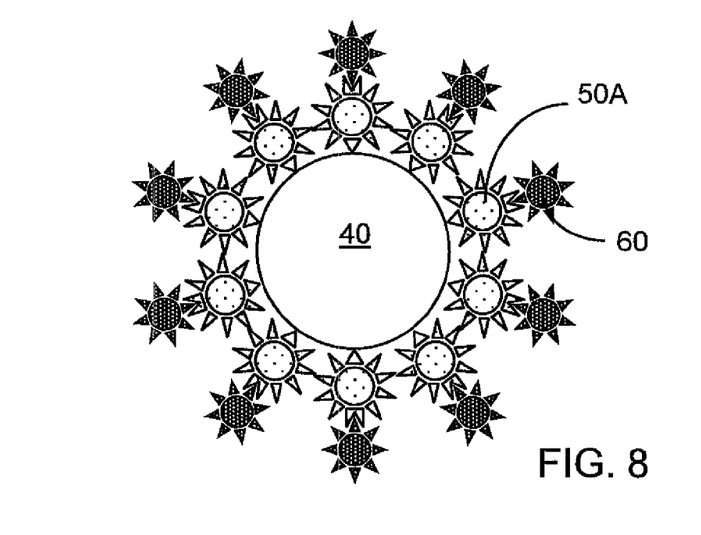
FIG. 8 is a schematic view showing atomic arrangement after charged molecules are bound to the semiconductor-functionalizing molecules of the chemical coating layer.

FIG. 8 illustrates the atomic arrangement after molecules 60 are bonded to the functionalizing molecules 50A of the chemical coating layer 50. Each charged molecule 50 is bonded to the first functional group 150A of a functionalizing molecule 50A. Upon bonding of the at least one type of chemical molecule 60 and the functional material of the chemical coating layer 50, the electronic charge distribution within the molecule 50A is altered. For example, the electric dielectric moment of the functionalizing molecule 50A, which is aligned in the direction perpendicular to the local surface of the semiconductor nanowire 40, may increase or decrease. Such increase or decrease in the electric dipole moment of the molecule 50A attracts or repels the charge carriers within the semiconductor nanowire 40. Because the lateral dimensions of the semiconductor nanowire 40 is typically on the order of 1 nm to 20 nm, such attraction or repulsion of the electrical charges in the semiconductor nanowire alters the free charge carrier density in the semiconductor nanowire 40. Thus, the bonding of chemical molecules 60 with the first functional group 150A of the molecule 50A has a direct impact on the charge carrier density in the semiconductor nanowire 40, and consequently on the conductivity of the semiconductor nanowire 40. By measuring the conductivity of the semiconductor nanowire 40, presence or concentration of the at least one type of chemical molecule is detected.

According to a first embodiment of the present invention, the exemplary semiconductor device of FIGS. 4A-4C is a chemical detector that detects the presence or concentration of at least one type of gas phase chemical molecule. The chemical coating layer 50 may comprise at least one functional material such as pyridine, dipyridine, or terpyridine. Such functional materials for the chemical coating layer 50 are self-aligned on the surface of the semiconductor nanowire such that the dipole moment of the functionalizing molecules are aligned perpendicular to the nearest surface of the semiconductor nanowire 40. The functional material bonds with at least one type of chemical molecule and the free charge carrier density in the semiconductor nanowire 40 is altered upon bonding of the at least one type of chemical molecule and the functional material. For example, the chemical molecule may be trinitrotoluene (TNT) in gas phase, which is present around a solid phase explosive or a liquid phase explosive including trinitrotoluene. The exemplary semiconductor device may thus be employed to detect explosives in a non-invasive manner.

Figure 9:
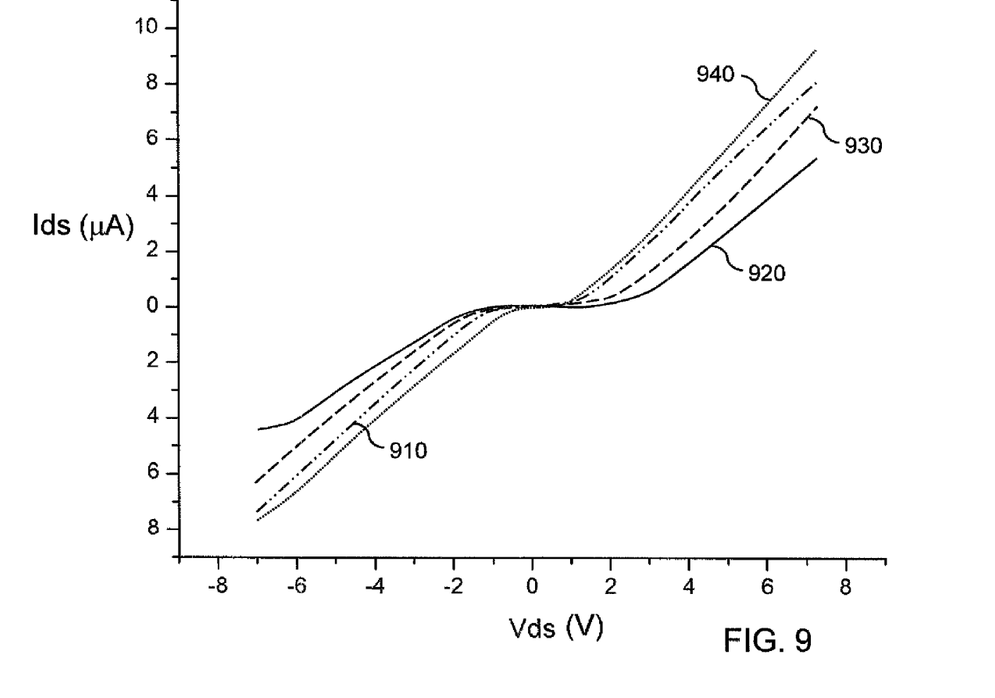
FIG. 9 is a graph illustrating the operation of the semiconductor nanowire device of the present invention. Electrical current through the semiconductor nanowire is shown under electrical bias after various types of surface treatment upon the semiconductor nanowire or the surface coating layer.

FIG. 9 is a graph illustrating the operation of the semiconductor nanowire device of the present invention. A first voltage-current curve 910 represents electrical current through the semiconductor nanowire 40 of FIGS. 3A-3C, i.e., the semiconductor nanowire device of the present invention without the chemical coating layer 50. The semiconductor material in this case is single crystalline silicon. To insure that no contaminants or native oxide layer is present on the surface of the semiconductor nanowire, the surface of the semiconductor nanowire 40 may be treated with a hydrofluoric acid (HF) solution. Under such conditions, the semiconductor nanowire device of FIGS. 3A-3C display the voltage-current characteristics represented by the first voltage-current curve 910.

A second voltage-current curve 920 represents electrical current through the semiconductor nanowire 40 of FIGS. 4A-4C. In this case, the chemical coating layer 50 includes a monolayer of terpyridine formed by dipping the semiconductor nanowire device of FIGS. 3A-3C into a solution of terpyridine. Alternately, the chemical coating layer 50 of terpyridine may be formed by any other method of applying a thin coating of terpyridine. In this example, the semiconductor nanowire 40 includes a p-doped single crystalline silicon. The terpyridine layer bound to silicon has a net negative charge and attracts the holes in the semiconductor nanowire 40 so that the free charge carrier density in the semiconductor nanowire decreases. Thus, the electrical current through the semiconductor nanowire 40 decreases upon formation of the chemical coating layer 50 of the monolayer of terpyridine.

A third voltage-current curve 930 represents electrical current through the semiconductor nanowire 40 of FIGS. 4A-4C after dipping in a copper sulfate ($CuSO_4$) solution. The chemical coating layer 50 includes a monolayer of terpyridine, which may be formed by dipping the semiconductor nanowire device of FIGS. 3A-3C into a solution of terpyridine. The semiconductor nanowire 40 includes a p-doped single crystalline silicon. After rinsing the surface of the semiconductor nanowire 40 with ammonia to remove any impurities, the surface of the chemical coating layer is dipped in the copper sulfate solution. Weakly bound hydrogen ions are formed on the surface of the chemical coating layer 50 after dipping. The weakly bound hydrogen ions constitute chemical molecules that are bonded to the monolayer of terpyridine. In general, such weak bonding may also be induced by treatment of the chemical coating layer 50 with an ionic salt solution. Each weakly bonded hydrogen ion provides a positive charge on the first functional group 150A of a molecule 50A (See FIG. 8). The positive charge reduces the attraction of the holes from the p-doped silicon toward the second functional group 250A of the functionalizing molecule 50A (See FIG. 8). Thus, more holes are available in the p-doped silicon, thereby increasing the conductivity of the semiconductor nanowire 40.

A fourth voltage-current curve 940 represents electrical current through the semiconductor nanowire 40 of FIGS. 4A-4C after dipping in a hydrogen chloride (HCl) solution. The chemical coating layer 50 includes a monolayer of terpyridine, which may be formed by dipping the semiconductor nanowire device of FIGS. 3A-3C into a solution of terpyridine. The semiconductor nanowire 40 includes a p-doped single crystalline silicon. A strongly bound hydrogen ions are formed on the surface of the chemical coating layer 50 after dipping in the hydrochloric acid solution. The strongly bound hydrogen ions constitute chemical molecules that are bonded to the monolayer of terpyridine. Each strongly bonded hydrogen ion provides a positive charge on the first functional group 150A of a functionalizing molecule 50A (See FIG. 8). The positive charge reduces the attraction of the holes from the p-doped silicon toward the second functional group 250A of the molecule 50A (See FIG. 8). Thus, more holes are available in the p-doped silicon, thereby increasing the conductivity of the semiconductor nanowire 40. Since the strong bonding of the hydrogen atoms effectively provide more positive charge to the chemical coating layer 50, the more holes are repelled into the semiconductor nanowire than the case of weakly bonded hydrogen atoms. Thus, the increase in the conductivity of the semiconductor nanowire 40 is greater than the case of the weakly bonded hydrogen atoms represented by the third voltage-current curve 930.

According to a second embodiment of the present invention, the exemplary semiconductor device of FIGS. 4A-4C is a chemical detector that detects the presence or concentration of at least one type of liquid phase chemical molecule. The chemical coating layer 50 may comprise at least one functional material such as a boronic acid. In general, an acid molecule may be employed as the functionalizing molecule of the chemical coating layer 50. As in the first embodiment, such functional materials for the chemical coating layer 50 are self-aligned on the surface of the semiconductor nanowire such that the dipole moment of the functionalizing molecules are aligned perpendicular to the nearest surface of the semiconductor nanowire 40. The functional material bonds with at least one type of chemical molecule and the free charge carrier density in the semiconductor nanowire 40 is altered upon bonding of the at least one type of chemical molecule and the functional material. For example, the chemical molecule may be saccharide (such as glucose or fructose) or a glycoprotein (such as a cancer marker) which is present in blood. The exemplary semiconductor device may thus be employed to detect the presence or quantity of glucose or fructose in blood or for cancer detection.

Figure 10:
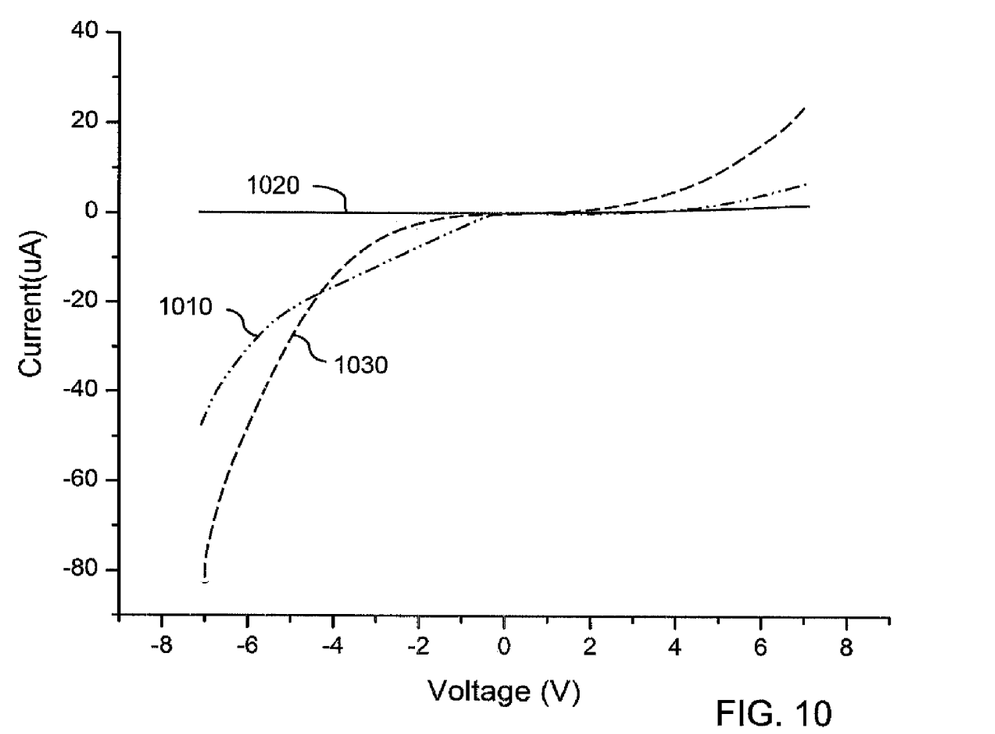
FIG. 10 is a graph of current through the semiconductor nanowire under electrical bias for bare silicon, after application of a chemical coating layer, and after exposure to a fructose solution.

FIG. 10 is another graph of current through the semiconductor nanowire under electrical bias for bare silicon, after application of a chemical coating layer, and after exposure to a fructose solution. A first voltage-current curve 1010 represents electrical current through the semiconductor nanowire 40 of FIGS. 3A-3C, i.e., the semiconductor nanowire device of the present invention without the chemical coating layer 50. The semiconductor material in this case is single crystalline silicon. To insure that no contaminants or native oxide layer is present on the surface of the semiconductor nanowire, the surface of the semiconductor nanowire 40 may be treated with a hydrofluoric acid (HF) solution. Under such conditions, the semiconductor nanowire device of FIGS. 3A-3C display the voltage-current characteristics represented by the first voltage-current curve 1010.

A second voltage-current curve 1020 represents electrical current through the semiconductor nanowire 40 of FIGS. 4A-4C. In this case, the chemical coating layer 50 includes a layer of a boronic acid, which may be formed by dipping the semiconductor nanowire device of FIGS. 3A-3C into a solution containing a boronic acid. Alternately, the chemical coating layer 50 of a boronic acid. In this example, the semiconductor nanowire 40 includes a intrinsic single crystalline silicon with heavily p-doped pads 20 and 30. A boronic acid layer attracts the electrons in the semiconductor nanowire 40 so that the free charge carrier density in the semiconductor nanowire decreases. Thus, the electrical current through the semiconductor nanowire 40 decreases upon formation of the chemical coating layer 50 of the monolayer of boronic acid.

A third voltage-current curve 1030 represents electrical current through the semiconductor nanowire 40 of FIGS. 4A-4C after dipping in a fructose solution. The chemical coating layer 50 includes a layer of a boronic acid, which may be formed by dipping the semiconductor nanowire device of FIGS. 3A-3C into a solution containing a boronic acid. The semiconductor nanowire 40 includes a p-doped single crystalline silicon. A strongly bound fructose molecules are formed on the surface of the chemical coating layer 50 after dipping in a sample solution including fructose. In one case, the sample solution may be blood. The strongly bound fructose ions constitute chemical molecules that are bonded to the chemical coating layer 50. Each fructose ion provides a negative charge on the first functional group 150A of a molecule 50A (See FIG. 8). The negative charge reduces the attraction of the electrons from the effectively n-doped silicon toward the second functional group 250A of the molecule 50A (See FIG. 8). Thus, more electrons are available in the n-doped silicon, thereby increasing the conductivity of the semiconductor nanowire 40. The increase in the conductivity of the semiconductor nanowire 40 may be measured to determine the amount of fructose in the sample solution.

While the present invention is described employing an embodiment in which the chemical coating layer 50 is formed after the formation of the first and second contact structures (28, 38), embodiments in which the chemical coating layer 50 is formed prior to the formation of the first and second contact structures (28, 38) are explicitly contemplated herein. Further, instead of employing a single semiconductor nanowire 40, the present invention may be practiced with a plurality of semiconductor nanowires 40 that are connected in parallel to increase signal strength as a detector. Such variations are explicitly contemplated herein.

While the invention has been described in terms of specific embodiments, it is evident in view of the foregoing description that numerous alternatives, modifications and variations will be apparent to those skilled in the art. Accordingly, the invention is intended to encompass all such alternatives, modifications and variations which fall within the scope and spirit of the invention and the following claims.

What is claimed is:

1. A semiconductor device comprising:
    a semiconductor nanowire, a first semiconductor pad located on a substrate and comprising a semiconductor material;
    a first semiconductor pad located on said substrate and laterally contacting a first end portion of said semiconductor nanowire;
    a second semiconductor pad located on said substrate and laterally contacting a second end portion of said semiconductor nanowire, wherein said semiconductor material of said semiconductor nanowire contiguously extends from said first end to said second end, and has a same dopant concentration between said first end and said second end; and
    a chemical coating layer located on said semiconductor nanowire and comprising a functional material that bonds with at least one type of charged molecule, wherein free charge carrier density in said semiconductor nanowire is altered upon bonding of said at least one type of charged molecule and said functional material.

2. The semiconductor device of claim 1, wherein said semiconductor nanowire comprises a p-doped semiconductor material and said free charge carrier density is substantially the same as a density of holes in said p-doped semiconductor material.

3. The semiconductor device of claim 1, wherein said semiconductor nanowire comprises an n-doped semiconductor material and said free charge carrier density is substantially the same as a density of electrons in said n-doped semiconductor material.

4. The semiconductor device of claim 1, wherein said semiconductor nanowire comprises an intrinsic semiconductor material and said free charge carrier density is substantially the same as a density of electrons and holes in said intrinsic semiconductor material.

5. The semiconductor device of claim 4, further comprising an insulator layer located in said substrate and vertically abutting said first semiconductor pad and said second semiconductor pad.

6. The semiconductor device of claim 4, wherein said semiconductor nanowire is suspended over said substrate and does not directly contact said substrate.

7. The semiconductor device of claim 4, wherein said chemical coating layer, said first semiconductor pad, and said second semiconductor pad encapsulate said semiconductor nanowire.

8. The semiconductor device of claim 7, wherein said functionalizing molecule includes another functional group located in closer proximity to said semiconductor nanowire than said functional group in said functionalizing molecule.

9. The semiconductor device of claim 7, wherein said chemical coating layer is a monolayer of said functionalizing molecule.

10. The semiconductor device of claim 7, wherein said functionalizing molecule is one of pyridine, dipyridine, terpyridine, and a boronic acid.

11. The semiconductor device of claim 7, wherein said functionalizing molecule is a molecule that selectively attaches to the nanowire semiconductor material with one group and has another functional group available to bind to charged species of interest.

12. The semiconductor device of claim 1, wherein said functional material includes a functionalizing molecule that is self-aligned on the nanowire semiconductor material in said chemical coating layer, wherein a functional group in said functionalizing molecule is exposed on an exterior surface of said chemical coating layer, and wherein said functional group bonds with said at least one type of charged molecule.

13. The semiconductor device of claim 12, wherein a direction along said functional group and said another functional group in said functionalizing molecule is a radial direction from a coaxial center line of said semiconductor nanowire.

14. The semiconductor device of claim 1, wherein an entirety of said first and second semiconductor pads and said silicon nanowire have a same dopant concentration throughout, and said chemical coating layer contiguously extends from said first semiconductor pad, around said silicon nanowire, and to said second semiconductor pad, and contacts all semiconductor surfaces of said first semiconductor pad, said second semiconductor pad, and said silicon nanowire.

15. A chemical detector comprising:
    a semiconductor nanowire located on a substrate and comprising a semiconductor material;
    a first semiconductor pad located on said substrate and laterally contacting a first end portion of said semiconductor nanowire;
    a second semiconductor pad located on said substrate and laterally contacting a second end portion of said semiconductor nanowire, wherein said semiconductor material of said semiconductor nanowire contiguously extends from said first end to said second end, and has a same dopant concentration between said first end and said second end; and
    a chemical coating layer located on said semiconductor nanowire and comprising a functional material that bonds with at least one type of chemical molecule, wherein free charge carrier density in said semiconductor nanowire is altered upon bonding of said at least one type of chemical molecule and said functional material, and wherein presence or concentration of said at least one type of chemical molecule is detected by measuring conductivity of said semiconductor nanowire.

16. The chemical detector of claim 15, wherein said at least one type of chemical molecule includes at least one type of gas phase chemical molecule.

17. The chemical detector of claim 15, wherein said at least one type of gas phase chemical molecule is trinitrotoluene (TNT), and wherein said chemical coating layer comprises at least one of pyridine, dipyridine, and terpyridine.

18. The chemical detector of claim 17, wherein said at least one type of liquid phase chemical molecule comprises at least one of a saccharide or a glycoprotein, and wherein said chemical coating layer comprises at least one of a boronic acid.

19. The chemical detector of claim 15, wherein said at least one type of chemical molecule includes at least one type of liquid phase chemical molecule.

20. The chemical detector of claim 15, wherein an entirety of said first and second semiconductor pads and said silicon nanowire have a same dopant concentration throughout, and said chemical coating layer contiguously extends from said first semiconductor pad, around said silicon nanowire, and to said second semiconductor pad, and contacts all semiconductor surfaces of said first semiconductor pad, said second semiconductor pad, and said silicon nanowire.

* * * * *